United States Patent [19]

Lehne et al.

[11] Patent Number: 5,477,575
[45] Date of Patent: Dec. 26, 1995

[54] PATIENT SUPPORT MECHANISM FOR MEDICAL EXAMINATION APPARATUS

[75] Inventors: Dietmar Lehne, Poxdorf; Werner Rogalsky, Langensendelbach, both of Germany

[73] Assignee: Siemens Aktiengesellschaft, Munich, Germany

[21] Appl. No.: 327,900

[22] Filed: Oct. 27, 1994

[30] Foreign Application Priority Data

Dec. 1, 1993 [DE] Germany ............... 43 40 960.1

[51] Int. Cl.⁶ .................................................. A47B 13/00
[52] U.S. Cl. ........................................ 5/601; 5/600; 5/511
[58] Field of Search .............................. 5/600, 601, 611,
5/510, 511, 81.1; 378/208, 209; 296/20

[56] References Cited

U.S. PATENT DOCUMENTS 1,742,309  1/1930  Flanagan ....................... 296/20
3,851,870  12/1974  Cook ............................. 5/601
4,576,368  3/1986  Ogawa .......................... 5/601

FOREIGN PATENT DOCUMENTS 97086  12/1983  European Pat. Off. .......... 5/600
150254  8/1985  European Pat. Off. .......... 5/600
3034932  4/1983  Germany .
1577766  7/1990  U.S.S.R. ..................... 378/209

*Primary Examiner*—Flemming Saether
*Attorney, Agent, or Firm*—Hill, Steadman & Simpson

[57] ABSTRACT

The patient support mechanism has a stationary lower part having a first ramp that ascends toward an examination space of the examination apparatus, an essentially horizontal, first section, a second ramp that proceeds essentially parallel to the first ramp, and an essentially horizontal second section that lies in the region of the examination space. An upper part having a bearing surface for a patient is displaceable on the lower part in the longitudinal direction thereof, whereby the upper part is lifted via the two ramps into the level of the examination space upon displacement of the upper part.

14 Claims, 4 Drawing Sheets

1

PATIENT SUPPORT MECHANISM FOR MEDICAL EXAMINATION APPARATUS

BACKGROUND OF THE INVENTION

1. Field of the Invention

The present invention is directed to a mechanism for a patient support of the type used to support a patient when conducting a medical examination.

2. Description of the Prior Art

Particularly for a tomographic examination system such as a CT and/or MR apparatus, a patient to be examined must be moved with a patient bearing mechanism into a cylindrical patient opening. The bottom of this opening in MR and CT apparatuses typically is at a height of between 900 and 1200 mm above the floor. If only longitudinal displaceability of the patient bearing mechanism were provided, it would not be especially comfortable for patients to be placed on such a patient bearing mechanism, particularly in the case of patients having limited freedom of movement. For this reason, patient bearing devices for, for example, tomography apparatuses, are usually adjustable not only in the longitudinal direction but also in height. Two separate drive mechanisms are provided for this purpose. German OS 30 34 932 discloses such a patient support mechanism.

In most instances, known patient support mechanisms are secured to the tomography apparatus or are independently anchored to the floor. In the above-recited published German application, the patient support mechanism is implemented as a mobile table that can be docked at the tomograph. The patient generally lies on a plate that is moved into the examination space of the medical examination apparatus via rollers.

In all of the above-described systems, there is an unavoidable gap between the tomograph apparatus and the patient bearing mechanism, which disturbs the ease with which a patient support plate can be rolled when introducing the patient.

Mobile patent tables to be docked to the tomograph apparatus are complicated solutions when patients are prepared for the measurement on a table given throughput-optimized systems and are examined on a second table parallel thereto.

SUMMARY OF THE INVENTION

An object of the present invention is to provide a patient support mechanism for a medical examination apparatus which has a simple structure with high patient comfort and with which a simple calculation of the patient weight is possible.

This object is inventively achieved in a patient support mechanism having the following elements:

A stationary lower part is composed of the following sections as viewed in the direction toward the examination space: a first ramp ascending toward the examination space, a substantially horizontal, first section, a second ramp that proceeds essentially parallel to the first ramp, and a substantially horizontal, second section that lies in the region of the examination space.

An upper part is displaceable on the lower part at least in the longitudinal direction of the lower part. The upper part has a support surface for a patient and guide elements that are spaced in the longitudinal direction corresponding to the spacing between the two ramps and which have a height difference corresponding to the vertical spacing between the two horizontal sections.

Given this arrangement, only a single drive mechanism is needed for the horizontal and vertical movement of the patient support mechanism. Gaps that disturb the rolling ease can be avoided in a simple way. The upper part of the patient bearing mechanism can easily be lifted with the assistance of a simple gantry in order to be able to rapidly undertake a change of patient. As a result of the simple structure, it is economically possible to prepare patients from the measurement on a first upper part of the patient support and to examine the patients on a second upper part parallel thereto, and thus to optimize the patient throughput.

DESCRIPTION OF THE PREFERRED EMBODIMENTS

Figure 1:
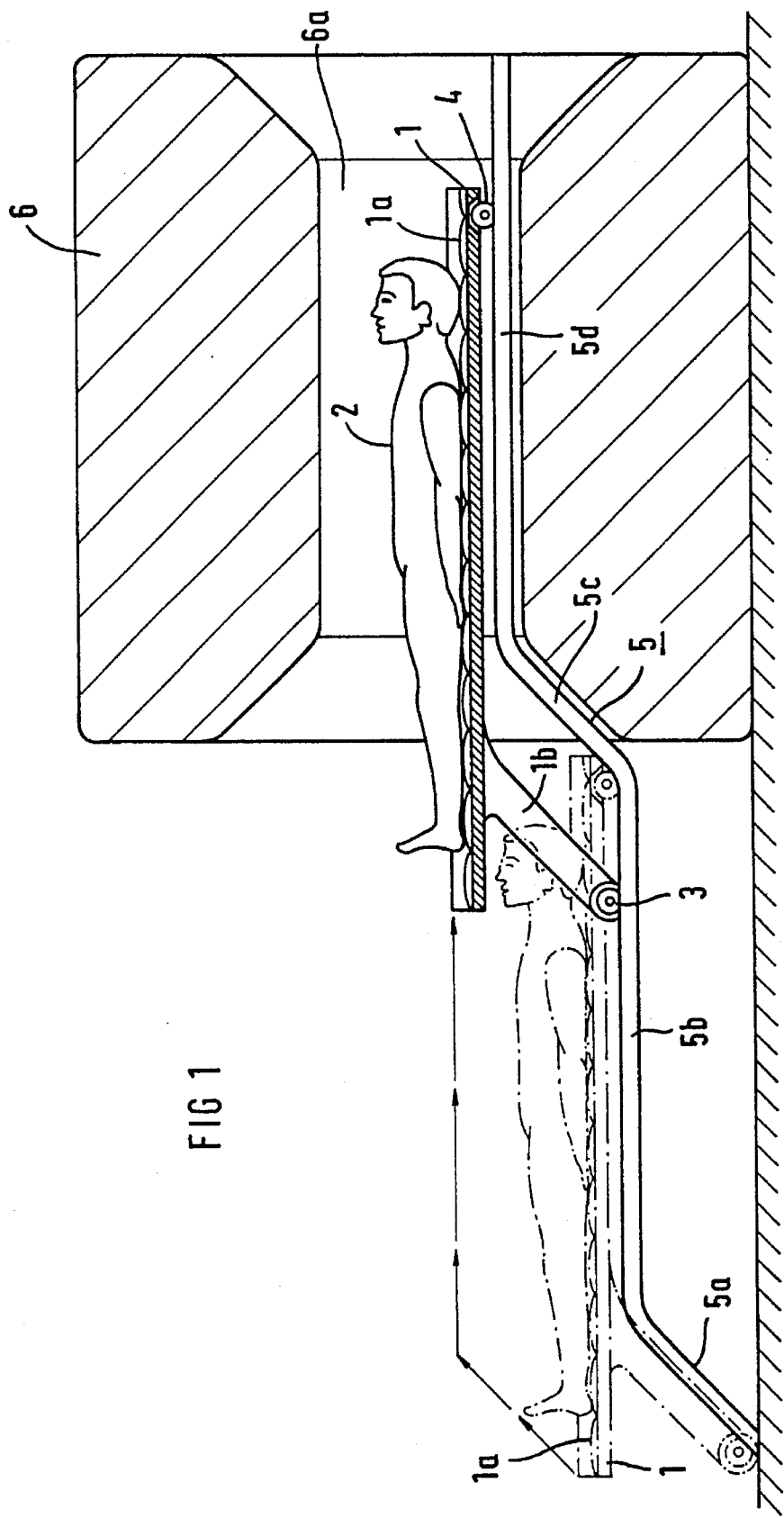
FIG. 1 is a side view of the patient support mechanism of the invention.
Figure 4:
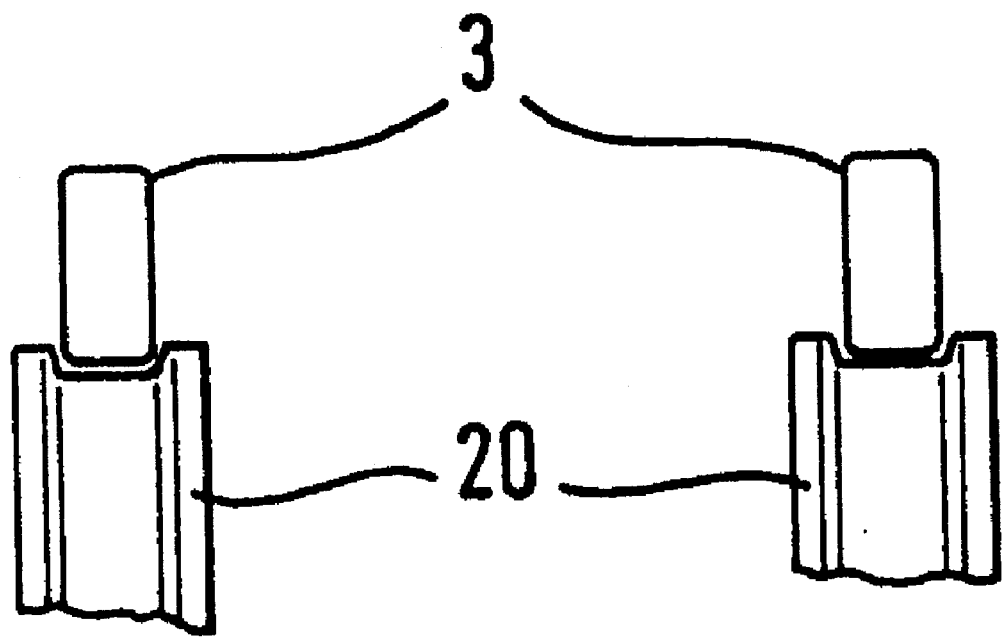
FIG. 4 shows an exemplary embodiment of guide profiles in the lower part for the patient support mechanism of the invention.

A nuclear magnetic resonance tomograph apparatus having an examination space $6a$ is schematically shown in the exemplary embodiment of FIG. 1. A patient bearing mechanism is composed of a stationary lower part 5 and an upper part 1 displaceable on the lower part 5 along the longitudinal direction of the lower part 5. The lower part 5 is composed of a first ramp $5a$, a first horizontal section $5b$, a second ramp $5c$, and a second horizontal section $5d$ that lies in the region of the examination space $6a$. The upper part 1 has rollers 3 and 4 with which, for example according to FIG. 4, it runs in guide profiles 20 of the lower part 5. The lower rollers 3 are thereby attached to a foot $1b$ such that the vertical spacing between the rollers 3 and the rollers 4 is equal to the vertical spacing between the horizontal sections $5b$ and $5d$. The spacing between the rollers 3 and 4 in the horizontal direction is equal to the spacing between the two ramps $5a$ and $5c$, likewise in the horizontal direction. It is thus assured that the upper part 1 always remains horizontal during the displacement in the horizontal direction.

A support surface 1 a for a patient 2 is arranged on the upper part 1.

The patient 2 is first placed on the support surface $1a$ in the position of the upper part 1 indicated with broken lines in FIG. 1. The bearing surface $1a$ is thereby in a relatively low position that, for example, enables a simple transfer of the patient from a hospital bed onto the bearing surface $1a$. Subsequently, the upper part together with the patient is introduced into the examination space $6a$. The rollers 4 and 5 thereby run in guide profiles 20 of the respective ramps $5c$ and $5a$, so that the upper part 1 together with the patient 2 is lifted to the height of the examination space $6a$. The patient 2 thereby always remains in a horizontal position. The lower part 5 is rigidly connected to the nuclear magnetic resonance tomograph apparatus 6, so that gaps in the guide profiles 20 can be avoided in a simple way, and thus a high degree of rolling ease is established. The longitudinal position of the patient 2 within the examination space 6a can be selected within broad limits by displacing the upper part 1. This is necessary both for a nuclear magnetic resonance tomography apparatus and for a computer tomography apparatus since only slice of the patient 2 that lie at least in the proximity of the center of the examination space 6a are imaged in both instances.

An important advantage of the illustrated arrangement is that only a single drive is required for the vertical movement and for the horizontal movement of the upper part 1, since the upper part 1 need only be pulled into or pulled out from the examination space 6a, whereby the vertical movement occurs on its own.

Figure 2:
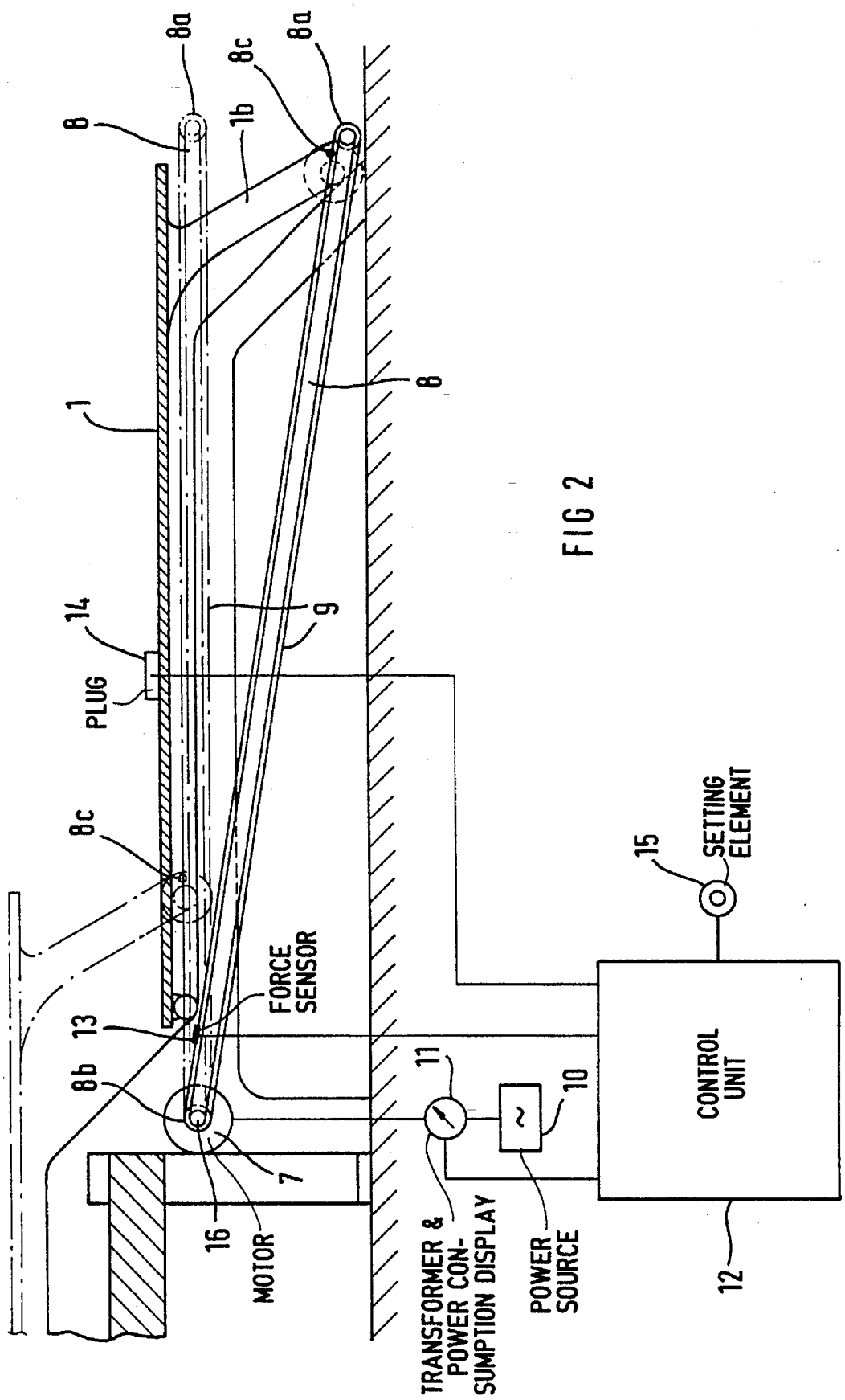
FIG. 2 is a longitudinal section of a first exemplary embodiment of a drive mechanism for the patient support mechanism of the invention.

FIG. 2 schematically shows an exemplary embodiment of a suitable drive. A rocker 8 is pivotable around a shaft 16 rigidly connected to the examination apparatus. This rocker 8 has rollers 8a and 8b at opposite ends around which a circulating element 9 runs. This element 9, for example, can be a belt, a chain or a cable. The element 9 is driven by a motor 7. The element 9 is connected to the upper part 1 at a point 8c at the lower end of the foot 1b.

Figure 3:
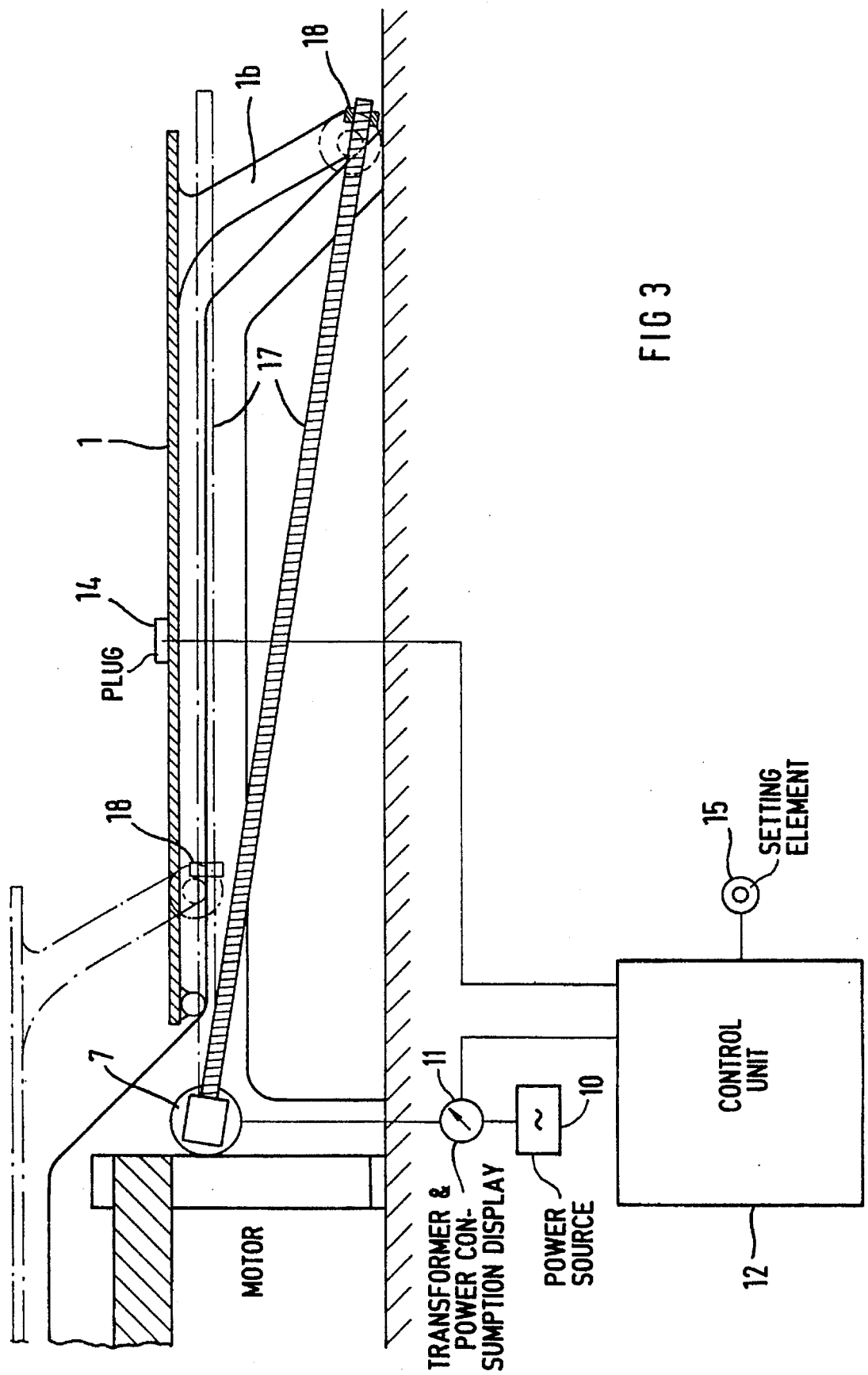
FIG. 3 is a longitudinal section of a second exemplary embodiment of a drive mechanism for the patient support mechanism of the invention.

The upper part 1 can thus be introduced into the examination space 6a with the assistance of the motor 7 by moving the point 8c in the direction of the examination space 6a. The rocker 8 also pivots upwardly together with the lifting of the upper part 1, ultimately into the position shown with broken lines in FIG. 2. Instead of the circulating element 9, a threaded spindle 17—as shown in FIG. 3—can be provided, this being turned by the motor 7 via a reversing gearing. A spindle nut 18 can then be connected to the lower end of the foot 1b, this spindle nut 18 moving along the longitudinal direction of the spindle given rotation of the spindle 17, and thereby displacing the upper part 1.

As is known, radio-frequency pulses are emitted into the patient for exciting the atoms in nuclear magnetic resonance tomography. An undesired but unavoidable side-effect is that the tissue is thereby heated. In order to keep this heating within safe limits, the radio-frequency power must observe specific maximum values. This maximum power is dependent on the body weight, and there are world-wide regulations regarding the allowable power per kilogram of body weight.

Contrast agents are employed in some instances both in nuclear magnetic resonance tomography as well as in computer tomography. The optimum quantity of contrast agent is often dependent on the body weight.

For the aforementioned reasons, the body weight of the patient must always be entered into the system before the examination given MR apparatus. In contrast agent studies, identifying the weight is also advantageous in the case of CT apparatuses. Heretofore, the patients were either weighed before the examination or the body weight was provided by the patient. Automatic weight calculations are known wherein the patient is weighed on the patient support mechanism of the examination apparatus. The outlay for this purpose given current designs is high since the support surface must either be seated on three or four load cells, or a play-free and friction-free bearing is required if load cells are not used.

The above-described inventive structure of the patient support mechanism enables a calculation of the body weight merely from the tensile force that is required to pull the upper part I together with the patient over the ramps 5a and 5c of the lower part 4. The generally required precision in the range of 5% can thereby be met since the friction occurring as a disturbance variable is low. Substantially only rolling friction occurs.

In order to identify the tensile force, a force-measuring sensor 13 for the tensile force can be built into the circulating element according to FIG. 2. The patient weight is then calculated from the measured tensile force in a control unit 12. Even more simply, the tensile force can be determined based on the power consumption of the motor 7, whereby a current transformer 11, which may have a display for the power consumption, is inserted between the power supply 10 and the motor 16. Non-linearities in the relationship between motor current and tensile force as well as voltage fluctuations can be taken into consideration with correction tables in the control unit 12.

Accessory parts such as, for example, coils or padding material are often also attached on the upper part 1 of the patient support mechanism. Since the weight of these accessory parts enters into the tensile force, this must be subtracted in the calculation of the patient weight. For example, this can be taken into consideration manually via a setting element 15 of the control unit 12. An automatic acquisition is also possible, particularly in the case of coils. Coils are generally connected via a plug 14. When coils are provided with a code for their weight, then the weight can be automatically recognized when the coil is plugged in.

An automatic and economic weight calculation with subsequent further processing is possible with this auxiliary to the patient support mechanism.

Although modifications and changes may be suggested by those skilled in the art, it is the intention of the inventors to embody within the patent warranted hereon all changes and modifications as reasonably and properly come within the scope of their contribution to the art.

We claim as our invention:

1. A patient support mechanism for use in introducing a patient into, and removing a patient from, a medical examination apparatus having an examination space, said patient support mechanism comprising:

a continuous stationary lower part having a plurality of integrated sections arranged in a sequence proceeding toward said examination space, said plurality of sections including, in sequence, a first ramp ascending toward said examination space, a substantially horizontal first section, a second ramp proceeding substantially parallel to said first ramp and ascending into said examination space, at a different level from said first ramp, and a substantially horizontal second section disposed in said examination space and vertically spaced higher than said first section, said lower part having a longitudinal direction extending into said examination space; and an upper part displaceable on said lower part along said longitudinal direction, said upper part having a supporting surface for a patient and a plurality of guide elements, said guide elements being spaced from each other in said longitudinal direction by a spacing corresponding to a spacing between said first and second ramps, and being spaced vertically from each other at different heights corresponding to said vertical spacing between said first and second horizontal sections.

2. A patient support mechanism as claimed in claim 1 wherein said upper part comprises a flat plate having a foot extending beneath said flat plate and facing away from said medical examination apparatus, with some guide elements in said plurality of guide elements being mounted at an end of said foot.

3. A patient support mechanism as claimed in claim 1 wherein said guide elements comprise rollers, and wherein said lower part has channels shaped to receive said rollers, said rollers rolling in said channels on said lower part as said upper part is moved into and out of said examination space.

4. A patient support mechanism as claimed in claim 1 further comprising drive means for displacing said upper part in said longitudinal direction.

5. A patient support mechanism as claimed in claim 4 wherein said drive means comprises a chain drive.

6. A patient support mechanism as claimed in claim 4 wherein said drive means comprises a belt drive.

7. A patient support mechanism as claimed in claim 4 wherein said drive means comprises a cable drive.

8. A patient support mechanism as claimed in claim 4 wherein said drive means comprises:

a rocker having a first end mounted for permitting pivoting of said rocker relative to said upper and lower parts, said rocker extending substantially in said longitudinal direction of said upper part;

a motor;

a circulating element drivingly engaging said motor and carried by said rocker, said circulating element being connected to said upper part at a side of said upper part facing away from said examination space.

9. A patient support mechanism as claimed in claim 1 further comprising drive means for moving said upper part into and out of said examination space, said drive means comprising:

a threaded spindle extending substantially in said longitudinal direction of said upper part and having a first end mounted for permitting vertical pivoting of said threaded spindle, said threaded spindle having a longitudinal axis and having a second end disposed at a region of said upper part facing away from said examination space;

means for rotating said threaded spindle around its longitudinal axis; and a spindle nut engaging said threaded spindle at said second end, said threaded nut being attached to said upper part for causing displacement of said upper part along said longitudinal direction as said threaded spindle is rotated in said spindle nut.

10. A patient support mechanism as claimed in claim 1 further comprising:

means for applying a tensile force to said upper part for moving said upper part over said first and second ramps; and means for calculating the weight of a patient disposed on said upper part by measuring said tensile force.

11. A patient support mechanism as claimed in claim 10 wherein said means for displacing includes a motor drive which consumes power due to the displacement of said upper part, and wherein said means for calculating the weight of a patient includes means for measuring said tensile force by measuring the power consumption of said motor drive.

12. A patient sport mechanism as claimed in claim 10 wherein said means for calculating the weight of a patient includes a force sensor for measuring said tensile force.

13. A patient sport mechanism as claimed in claim 10 further comprising:

at least one auxiliary component carried by said upper part and adding additional weight carried by said first part; and means for manually entering said additional weight into said means for calculating the weight of a patient, said means for calculating the weight of a patient including means for subtracting said additional weight from a weight calculated from measurement of said tensile force.

14. A patient support mechanism as claimed in claim 10 further comprising:

at least one auxiliary component carried on said upper part and adding additional weight carried by said first part;

sensor means for sensing said additional weight and supplying a signal corresponding to said additional weight to said means for calculating the weight of a patient; and said means for calculating the weight of a patient including means for subtracting said additional weight from a weight calculated from the measurement of said tensile force.

* * * * *